United States Patent [19]

Yamada et al.

[11] Patent Number: 5,731,176
[45] Date of Patent: Mar. 24, 1998

[54] DNA FRAGMENT ENCODING A POLYPEPTIDE HAVING NITRILE HYDRATASE ACTIVITY, A TRANSFORMANT CONTAINING THE GENE AND A PROCESS FOR THE PRODUCTION OF AMIDES USING THE TRANSFORMANT

[75] Inventors: Hideaki Yamada, 19-1, Matsugasaki, Kinomotocho, Sakyo-ku, Kyoto-shi, Kyoto-fu; Toru Nagasawa, Kyoto; Teruhiko Beppu, 5-21, Horinouchi 1-chome, Suginami-ku, Tokyo; Sueharu Horinouch, Tokyo; Makoto Nishiyama, Tokyo, all of Japan

[73] Assignees: Nitto Chemical Industry Co., Ltd.; Teruhiko Beppu; Hideaki Yamada, all of, Japan

[21] Appl. No.: 28,463

[22] Filed: Mar. 9, 1993

Related U.S. Application Data

[63] Continuation of Ser. No. 694,747, May 2, 1991, abandoned.

[51] Int. Cl.$^6$ .............. C12P 13/02; C12N 1/00; C12N 5/00; C12N 9/78; C12N 15/55; C12N 15/63
[52] U.S. Cl. .......... 435/129; 435/227; 435/320.1; 435/252.3; 435/325; 435/254.11; 435/172.3; 536/23

[58] Field of Search .............. 536/23.2; 435/69.1, 435/227, 252.3, 240.1, 874, 129, 325

[56] References Cited

PUBLICATIONS

Nagasawa et al., "Nitrile Hydratase–Catalyzed Production of Nicotinamide from 3–Cyanopyridine in *Rhodococcus rhodocrous* J1" Appl. Env. Microbiol. (1988) 54(7):1766–1769.

Nishiyama et al., "Cloning and Characterization of genes Responsible for the Metabolism of Nitrile Compounds from *Pseudomonas chlororaphis* B23" J. Bacteriol., (1991) 173(8):2465–2472.

*Primary Examiner*—Robert A. Wax
*Assistant Examiner*—Gabriele E. Bugaisky
*Attorney, Agent, or Firm*—Pennie & Edmonds

[57] ABSTRACT

The present invention has disclosed the amino acid sequence and nucleotide sequence of the α- and β-subunits of two types of nitrile hydratase derived from *Rhodococcus rhodochrous* J-1. The DNA fragment encoding nitrile hydratase is inserted into an expression vector and the recombinant vector is used for transformation. The transformant contains multiple copies of the gene and can produce much higher level of nitrile hydratase compared with conventionally used microorganisms.

14 Claims, 1 Drawing Sheet

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 203 amino acids
        ( B ) TYPE: amino acid
        ( C ) STRANDEDNESS: single
        ( D ) TOPOLOGY: linear     ( i i ) MOLECULE TYPE: peptide     ( v i ) ORIGINAL SOURCE:
        ( A ) ORGANISM: Rhodococcus rhodochorus
        ( B ) STRAIN: J-1 (FERM BP-1478)

( x i ) SEQUENCE DESCRIPTION: SEQ ID NO:1:

```
Met Ser Glu His Val Asn Lys Tyr Thr Glu Tyr Glu Ala Arg Thr Lys
 1               5                  10                  15

Ala Ile Glu Thr Leu Leu Tyr Glu Arg Gly Leu Ile Thr Pro Ala Ala
                20                  25                  30

Val Asp Arg Val Val Ser Tyr Tyr Glu Asn Glu Ile Gly Pro Met Gly
            35                  40                  45

Gly Ala Lys Val Val Ala Lys Ser Trp Val Asp Pro Glu Tyr Arg Lys
        50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
               100                 105                 110

Leu Gly Leu Pro Pro Ala Trp Tyr Lys Ser Met Glu Tyr Arg Ser Arg
            115                 120                 125
```

```
        Val   Val   Ala   Asp   Pro   Arg   Gly   Val   Leu   Lys   Arg   Asp   Phe   Gly   Phe   Asp
              130                     135                     140

Ile   Pro   Asp   Glu   Val   Glu   Val   Arg   Val   Trp   Asp   Ser   Ser   Ser   Glu   Ile
        145                           150                     155                                 160

Arg   Tyr   Ile   Val   Ile   Pro   Glu   Arg   Pro   Ala   Gly   Thr   Asp   Gly   Trp   Ser
                                165                     170                                 175

Glu   Glu   Glu   Leu   Thr   Lys   Leu   Val   Ser   Arg   Asp   Ser   Met   Ile   Gly   Val
                          180                           185                                 190

Ser   Asn   Ala   Leu   Thr   Pro   Gln   Glu   Val   Ile   Val
                    195                           200
```

( 2 ) INFORMATION FOR SEQ ID NO:2:

( i ) SEQUENCE CHARACTERISTICS:
        ( A ) LENGTH: 229 amino acids
        ( B ) TYPE: amino acid
        ( C ) STRANDEDNESS: single
        ( D ) TOPOLOGY: linear     ( i i ) MOLECULE TYPE: peptide     ( v i ) ORIGINAL SOURCE:
        ( A ) ORGANISM: Rhodococcus rhodochrous
        ( B ) STRAIN: J-1 (FERM BP-1478)

( x i ) SEQUENCE DESCRIPTION: SEQ ID NO:2:

```
        Met   Asp   Gly   Ile   His   Asp   Thr   Gly   Gly   Met   Thr   Gly   Tyr   Gly   Pro   Val
        1                       5                           10                                  15

Pro   Tyr   Gln   Lys   Asp   Glu   Pro   Phe   Phe   His   Tyr   Glu   Trp   Glu   Gly   Arg
                          20                          25                          30

Thr   Leu   Ser   Ile   Leu   Thr   Trp   Met   His   Leu   Lys   Gly   Ile   Ser   Trp   Trp
                    35                          40                          45

Asp   Lys   Ser   Arg   Phe   Phe   Arg   Glu   Ser   Met   Gly   Asn   Glu   Asn   Tyr   Val
              50                          55                          60

Asn   Glu   Ile   Arg   Asn   Ser   Tyr   Tyr   Thr   His   Trp   Leu   Ser   Ala   Ala   Glu
        65                          70                          75                              80

Arg   Ile   Leu   Val   Ala   Asp   Lys   Ile   Ile   Thr   Glu   Glu   Arg   Lys   His
                                85                          90                          95

Arg   Val   Gln   Glu   Ile   Leu   Glu   Gly   Arg   Tyr   Thr   Asp   Arg   Lys   Pro   Ser
                          100                         105                         110

Arg   Lys   Phe   Asp   Pro   Ala   Gln   Ile   Glu   Lys   Ala   Ile   Glu   Arg   Leu   His
                    115                         120                         125

Glu   Pro   His   Ser   Leu   Ala   Leu   Pro   Gly   Ala   Glu   Pro   Ser   Phe   Ser   Leu
              130                         135                         140

Gly   Asp   Lys   Ile   Lys   Val   Lys   Ser   Met   Asn   Pro   Leu   Gly   His   Thr   Arg
        145                         150                         155                             160

Cys   Pro   Lys   Tyr   Val   Arg   Asn   Lys   Ile   Gly   Glu   Ile   Val   Ala   Tyr   His
                                165                         170                             175

Gly   Cys   Gln   Ile   Tyr   Pro   Glu   Ser   Ser   Ser   Ala   Gly   Leu   Gly   Asp   Asp
                          180                         185                             190

Pro   Arg   Pro   Leu   Tyr   Thr   Val   Ala   Phe   Ser   Ala   Gln   Glu   Leu   Trp   Gly
                    195                         200                         205

Asp   Asp   Gly   Asn   Gly   Lys   Asp   Val   Val   Cys   Val   Asp   Leu   Trp   Glu   Pro
              210                         215                         220

Tyr   Leu   Ile   Ser   Ala
        225
```

( 2 ) INFORMATION FOR SEQ ID NO:3:

(i) SEQUENCE CHARACTERISTICS:
    (A) LENGTH: 207 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Rhodococcus rhodochrous
    (B) STRAIN: J-1 (FERM BP-1478)

(xi) SEQUENCE DESCRIPTION: SEQ ID NO:3:

| Met | Thr | Ala | His | Asn | Pro | Val | Gln | Gly | Thr | Leu | Pro | Arg | Ser | Asn | Glu |
|---|---|---|---|---|---|---|---|---|---|---|---|---|---|---|---|
| 1 | | | | 5 | | | | | 10 | | | | | 15 | |
| Glu | Ile | Ala | Ala | Arg | Val | Lys | Ala | Met | Glu | Ala | Ile | Leu | Val | Asp | Lys |
| | | | 20 | | | | | 25 | | | | | 30 | | |
| Gly | Leu | Ile | Ser | Thr | Asp | Ala | Ile | Asp | His | Met | Ser | Ser | Val | Tyr | Glu |
| | | | 35 | | | | 40 | | | | | 45 | | | |
| Asn | Glu | Val | Gly | Pro | Gln | Leu | Gly | Ala | Lys | Ile | Val | Ala | Arg | Ala | Trp |
| | 50 | | | | | 55 | | | | | 60 | | | | |
| Val | Asp | Pro | Glu | Phe | Lys | Gln | Arg | Leu | Leu | Thr | Asp | Ala | Thr | Ser | Ala |
| 65 | | | | | 70 | | | | | 75 | | | | | 80 |
| Cys | Arg | Glu | Met | Gly | Val | Gly | Gly | Met | Gln | Gly | Glu | Glu | Met | Val | Val |
| | | | | 85 | | | | | 90 | | | | | 95 | |
| Leu | Glu | Asn | Thr | Gly | Thr | Val | His | Asn | Met | Val | Val | Cys | Thr | Leu | Cys |
| | | | 100 | | | | | 105 | | | | | 110 | | |
| Ser | Cys | Tyr | Pro | Trp | Pro | Val | Leu | Gly | Leu | Pro | Pro | Asn | Trp | Tyr | Lys |
| | | 115 | | | | | 120 | | | | | 125 | | | |
| Tyr | Pro | Ala | Tyr | Arg | Ala | Arg | Ala | Val | Arg | Asp | Pro | Arg | Gly | Val | Leu |
| | 130 | | | | | 135 | | | | | 140 | | | | |
| Ala | Glu | Phe | Gly | Tyr | Thr | Pro | Asp | Pro | Asp | Val | Glu | Ile | Arg | Ile | Trp |
| 145 | | | | | 150 | | | | | 155 | | | | | 160 |
| Asp | Ser | Ser | Ala | Glu | Leu | Arg | Tyr | Trp | Val | Leu | Pro | Gln | Arg | Pro | Ala |
| | | | | 165 | | | | | 170 | | | | | 175 | |
| Gly | Thr | Glu | Asn | Phe | Thr | Glu | Glu | Gln | Leu | Ala | Asp | Leu | Val | Thr | Arg |
| | | | 180 | | | | | 185 | | | | | 190 | | |
| Asp | Ser | Leu | Ile | Gly | Val | Ser | Val | Pro | Thr | Thr | Pro | Ser | Lys | Ala | |
| | | 195 | | | | | 200 | | | | | 205 | | | |

(2) INFORMATION FOR SEQ ID NO:4:

(i) SEQUENCE CHARACTERISTICS:
    (A) LENGTH: 226 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Rhodococcus rhodochrous
    (B) STRAIN: J-1 (FERM BP-1478)

(xi) SEQUENCE DESCRIPTION: SEQ ID NO:4:

| Met | Asp | Gly | Ile | His | Asp | Leu | Gly | Gly | Arg | Ala | Gly | Leu | Gly | Pro | Ile |
|---|---|---|---|---|---|---|---|---|---|---|---|---|---|---|---|
| 1 | | | | 5 | | | | | 10 | | | | | 15 | |
| Lys | Pro | Glu | Ser | Asp | Glu | Pro | Val | Phe | His | Ser | Asp | Trp | Glu | Arg | Ser |
| | | | 20 | | | | | 25 | | | | | 30 | | |
| Val | Leu | Thr | Met | Phe | Pro | Ala | Met | Ala | Leu | Ala | Gly | Ala | Phe | Asn | Leu |
| | | | 35 | | | | 40 | | | | | 45 | | | |

|     |     |     |     |     |     |     |     |     |     |     |     |     |     |     |
| --- | --- | --- | --- | --- | --- | --- | --- | --- | --- | --- | --- | --- | --- | --- |
| Asp | Gln 50 | Phe | Arg | Gly | Ala | Met 55 | Glu | Gln | Ile | Pro | Pro 60 | His | Asp | Tyr | Leu |
| Thr 65 | Ser | Gln | Tyr | Tyr | Glu 70 | His | Trp | Met | His | Ala 75 | Met | Ile | His | His | Gly 80 |
| Ile | Glu | Ala | Gly | Ile 85 | Phe | Asp | Ser | Asp | Glu 90 | Leu | Asp | Arg | Arg | Thr 95 | Gln |
| Tyr | Tyr | Met | Asp 100 | His | Pro | Asp | Asp | Thr 105 | Thr | Pro | Thr | Arg | Gln 110 | Asp | Pro |
| Gln | Leu | Val 115 | Glu | Thr | Ile | Ser | Gln 120 | Leu | Ile | Thr | His | Gly 125 | Ala | Asp | Tyr |
| Arg | Arg 130 | Pro | Thr | Asp | Thr | Glu 135 | Ala | Ala | Phe | Ala | Val 140 | Gly | Asp | Lys | Val |
| Ile 145 | Val | Arg | Ser | Asp | Ala 150 | Ser | Pro | Asn | Thr | His 155 | Thr | Arg | Arg | Ala | Gly 160 |
| Tyr | Val | Arg | Gly | Arg 165 | Val | Gly | Glu | Val | Val 170 | Ala | Thr | His | Gly | Ala 175 | Tyr |
| Val | Phe | Pro | Asp 180 | Thr | Asn | Ala | Leu | Gly 185 | Ala | Gly | Glu | Ser | Pro 190 | Glu | His |
| Leu | Tyr | Thr 195 | Val | Arg | Phe | Ser | Ala 200 | Thr | Glu | Leu | Trp | Gly 205 | Glu | Pro | Ala |
| Ala | Pro 210 | Asn | Val | Val | Asn | His 215 | Ile | Asp | Val | Phe | Glu 220 | Pro | Tyr | Leu | Leu |
| Pro 225 | Ala |  |  |  |  |  |  |  |  |  |  |  |  |  |  |

( 2 ) INFORMATION FOR SEQ ID NO:5:

( i ) SEQUENCE CHARACTERISTICS:
        ( A ) LENGTH: 609 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Rhodococcus rhodochrous
        ( B ) STRAIN: J-1 (FERM BP-1478)

( x i ) SEQUENCE DESCRIPTION: SEQ ID NO:5:

| | | | | | |
|---|---|---|---|---|---|
| GTGAGCGAGC | ACGTCAATAA | GTACACGGAG | TACGAGGCAC | GTACCAAGGC | GATCGAAACC | 60 |
| TTGCTGTACG | AGCGAGGGCT | CATCACGCCC | GCCGCGGTCG | ACCGAGTCGT | TTCGTACTAC | 120 |
| GAGAACGAGA | TCGGCCCGAT | GGGCGGTGCC | AAGGTCGTGG | CCAAGTCCTG | GGTGGACCCT | 180 |
| GAGTACCGCA | AGTGGCTCGA | AGAGGACGCG | ACGGCCGCGA | TGGCGTCATT | GGGCTATGCC | 240 |
| GGTGAGCAGG | CACACCAAAT | TCGGCGGTC | TTCAACGACT | CCCAAACGCA | TCACGTGGTG | 300 |
| GTGTGCACTC | TGTGTTCGTG | CTATCCGTGG | CCGGTGCTTG | GTCTCCCGCC | CGCCTGGTAC | 360 |
| AAGAGCATGG | AGTACCGGTC | CCGAGTGGTA | GCGGACCCTC | GTGGAGTGCT | CAAGCGCGAT | 420 |
| TTCGGTTTCG | ACATCCCCGA | TGAGGTGGAG | GTCAGGGTTT | GGGACAGCAG | CTCCGAAATC | 480 |
| CGCTACATCG | TCATCCCGGA | ACGGCCGGCC | GGCACCGACG | GTTGGTCCGA | GGAGGAGCTG | 540 |
| ACGAAGCTGG | TGAGCCGGGA | CTCGATGATC | GGTGTCAGTA | ATGCGCTCAC | ACCGCAGGAA | 600 |
| GTGATCGTA | | | | | | 609 |

( 2 ) INFORMATION FOR SEQ ID NO:6:

( i ) SEQUENCE CHARACTERISTICS:
        ( A ) LENGTH: 687 base pairs (B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Rhodococcus rhodochrous
(B) STRAIN: J-1 (FERM BP-1478)

(xi) SEQUENCE DESCRIPTION: SEQ ID NO:6:

| | | | | | |
|---|---|---|---|---|---|
| ATGGATGGTA | TCCACGACAC | AGGCGGCATG | ACCGGATACG | GACCGGTCCC | CTATCAGAAG | 60
| GACGAGCCCT | TCTTCCACTA | CGAGTGGGAG | GGTCGGACCC | TGTCAATTCT | GACTTGGATG | 120
| CATCTCAAGG | GCATATCGTG | GTGGGACAAG | TCGCGGTTCT | TCCGGGAGTC | GATGGGGAAC | 180
| GAAAACTACG | TCAACGAGAT | TCGCAACTCG | TACTACACCC | ACTGGCTGAG | TGCGGCAGAA | 240
| CGTATCCTCG | TCGCCGACAA | GATCATCACC | GAAGAAGAGC | GAAAGCACCG | TGTGCAAGAG | 300
| ATCCTTGAGG | GTCGGTACAC | GGACAGGAAG | CCGTCGCGGA | AGTTCGATCC | GGCCCAGATC | 360
| GAGAAGGCGA | TCGAACGGCT | TCACGAGCCC | CACTCCCTAG | CGCTTCCAGG | AGCGGAGCCG | 420
| AGTTTCTCTC | TCGGTGACAA | GATCAAAGTG | AAGAGTATGA | ACCCGCTGGG | ACACACACGG | 480
| TGCCCGAAAT | ATGTGCGGAA | CAAGATCGGG | GAAATCGTCG | CCTACCACGG | CTGCCAGATC | 540
| TATCCCGAGA | GCAGCTCCGC | CGGCCTCGGC | GACGATCCTC | GCCCGCTCTA | CACGGTCGCG | 600
| TTTTCCGCCC | AGGAACTGTG | GGGCGACGAC | GGAAACGGGA | AGACGTAGT | GTGCGTCGAT | 660
| CTCTGGGAAC | CGTACCTGAT | CTCTGCG | | | | 687

(2) INFORMATION FOR SEQ ID NO:7:

(i) SEQUENCE CHARACTERISTICS:
(A) LENGTH: 621 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Rhodococcus rhodochrous
(B) STRAIN: J-1 (FERM BP-1478)

(xi) SEQUENCE DESCRIPTION: SEQ ID NO:7:

| | | | | | |
|---|---|---|---|---|---|
| ATGACCGCCC | ACAATCCCGT | CCAGGGCACG | TTGCCACGAT | CGAACGAGGA | GATCGCCGCA | 60
| CGCGTGAAGG | CCATGGAGGC | CATCCTCGTC | GACAAGGGCC | TGATCTCCAC | CGACGCCATC | 120
| GACCACATGT | CCTCGGTCTA | CGAGAACGAG | GTCGGTCCTC | AACTCGGCGC | CAAGATCGTC | 180
| GCCCGCGCCT | GGGTCGATCC | CGAGTTCAAG | CAGCGCCTGC | TCACCGACGC | CACCAGCGCC | 240
| TGCCGTGAAA | TGGGCGTCGG | CGGCATGCAG | GGCGAAGAAA | TGGTCGTGCT | GGAAAACACC | 300
| GGCACGGTCC | ACAACATGGT | CGTATGTACC | TTGTGCTCGT | GCTATCCGTG | GCCGGTTCTC | 360
| GGCCTGCCAC | CCAACTGGTA | CAAGTACCCC | GCCTACCGCG | CCCGCGCTGT | CCGCGACCCC | 420
| CGAGGTGTGC | TGGCCGAATT | CGGATATACC | CCCGACCCTG | ACGTCGAGAT | CCGGATATGG | 480
| GACTCGAGTG | CCGAACTTCG | CTACTGGGTC | CTGCCGCAAC | GCCCAGCCGG | CACCGAGAAC | 540
| TTCACCGAAG | AACAACTCGC | CGACCTCGTC | ACCCGCGACT | CGCTCATCGG | CGTATCCGTC | 600
| CCCACCACAC | CCAGCAAGGC | C | | | | 621

(2) INFORMATION FOR SEQ ID NO:8:

(i) SEQUENCE CHARACTERISTICS:
(A) LENGTH: 678 base pairs

```
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Rhodococcus rhodochrous
            ( B ) STRAIN: J-1 (FERM BP-1478)

( x i ) SEQUENCE DESCRIPTION: SEQ ID NO:8:
```

| | | | | | |
|---|---|---|---|---|---|
| ATGGATGGAA | TCCACGACCT | CGGTGGCCGC | GCCGGCCTGG | GTCCGATCAA | GCCCGAATCC | 60
| GATGAACCTG | TTTTCCATTC | CGATTGGGAG | CGGTCGGTTT | TGACGATGTT | CCCGGCGATG | 120
| GCGCTGGCCG | GCGCGTTCAA | TCTCGACCAG | TTCCGGGGCG | CGATGGAGCA | GATCCCCCCG | 180
| CACGACTACC | TGACCTCGCA | ATACTACGAG | CACTGGATGC | ACGCGATGAT | CCACCACGGC | 240
| ATCGAGGCGG | GCATCTTCGA | TTCCGACGAA | CTCGACCGCC | GCACCCAGTA | CTACATGGAC | 300
| CATCCGGACG | ACACGACCCC | CACGCGGCAG | GATCCGCAAC | TGGTGGAGAC | GATCTCGCAA | 360
| CTGATCACCC | ACGGAGCCGA | TTACCGACGC | CCGACCGACA | CCGAGGCCGC | ATTCGCCGTA | 420
| GGCGACAAAG | TCATCGTGCG | GTCGGACGCC | TCACCGAACA | CCCACACCCG | CCGCGCCGGA | 480
| TACGTCCGCG | GTCGTGTCGG | CGAAGTCGTG | GCGACCCACG | GCGCGTATGT | CTTTCCGGAC | 540
| ACCAACGCAC | TCGGCGCCGG | CGAAAGCCCC | GAACACCTGT | ACACCGTGCG | GTTCTCGGCG | 600
| ACCGAGTTGT | GGGGTGAACC | TGCCGCCCCG | AACGTCGTCA | ATCACATCGA | CGTGTTCGAA | 660
| CCGTATCTGC | TACCGGCC | | | | | 678

```
( 2 ) INFORMATION FOR SEQ ID NO:9:

( i ) SEQUENCE CHARACTERISTICS:
            ( A ) LENGTH: 26 amino acids
            ( B ) TYPE: amino acid
            ( C ) STRANDEDNESS: single
            ( D ) TOPOLOGY: linear ( i i ) MOLECULE TYPE: peptide ( v i ) ORIGINAL SOURCE:
            ( A ) ORGANISM: Rhodococcus rhodochrous
            ( B ) STRAIN: J-1 (FERM BP-1478)

( x i ) SEQUENCE DESCRIPTION: SEQ ID NO:9:

Ser  Glu  His  Val  Asn  Lys  Tyr  Thr  Glu  Tyr  Glu  Ala  Arg  Thr  Lys  Ala
    1                   5                        10                       15

Ile  Glu  Thr  Leu  Leu  Tyr  Glu  Arg  Gly  Leu
                        20                   25

( 2 ) INFORMATION FOR SEQ ID NO:10:

( i ) SEQUENCE CHARACTERISTICS:
            ( A ) LENGTH: 28 amino acids
            ( B ) TYPE: amino acid
            ( C ) STRANDEDNESS: single
            ( D ) TOPOLOGY: linear ( i i ) MOLECULE TYPE: peptide ( v i ) ORIGINAL SOURCE:
            ( A ) ORGANISM: Rhodococcus rhodochrous
            ( B ) STRAIN: J-1 (FERM BP-1478)

( x i ) SEQUENCE DESCRIPTION: SEQ ID NO:10:

Met  Asp  Gly  Ile  His  Asp  Thr  Gly  Gly  Met  Thr  Gly  Tyr  Gly  Pro  Val
    1                   5                        10                       15

Pro  Tyr  Gln  Lys  Asp  Glu  Pro  Phe  Phe  His  Tyr  Glu
```

20

25

(2) INFORMATION FOR SEQ ID NO:11:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Rhodococcus rhodochrous
    (B) STRAIN: J-1 (FERM BP-1478)

(xi) SEQUENCE DESCRIPTION: SEQ ID NO:11:

```
Thr Ala His Asn Pro Val Gln Gly Thr Leu Pro Arg Xaa Asn Glu
 1               5                  10                  15
```

(2) INFORMATION FOR SEQ ID NO:12:

(i) SEQUENCE CHARACTERISTICS:
    (A) LENGTH: 19 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Rhocococcus rhodochrous
    (B) STRAIN: J-1 (FERM BP-1478)

(xi) SEQUENCE DESCRIPTION: SEQ ID NO:12:

```
Met Asp Gly Ile His Asp Leu Gly Gly Arg Ala Xaa Leu Xaa Pro Ile
 1               5                  10                  15

Lys Pro Glu
```

(2) INFORMATION FOR SEQ ID NO:13:

(i) SEQUENCE CHARACTERISTICS:
    (A) LENGTH: 2070 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Rhodococcus sp.
    (B) STRAIN: N-774 (FERM BP-1936)

(ix) FEATURE:
    (A) NAME/KEY: CDS
    (B) LOCATION: 675..1295

(ix) FEATURE:
    (A) NAME/KEY: CDS
    (B) LOCATION: 1325..1960

(xi) SEQUENCE DESCRIPTION: SEQ ID NO:13:

```
GCATGCTTTC CACATCTGGA ACGTGATCGC CACGGACGGT GGTGCCTACC AGATGTTGGA    60

CGGCAACGGA TACGGCATGA ACGCCGAAGG TTTGTACGAT CCGGAACTGA TGGCACACTT   120

TGCTTCTCGA CGCATTCAGC ACGCCGACGC TCTGTCCGAA ACCGTCAAAC TGGTGGCCCT   180

GACCGGCCAC CACGGCATCA CCACCCTCGG CGGCGCGAGC TACGGCAAAG CCCGGAACCT   240

CGTACCGCTT GCCCGCGCCG CCTACGACAC TGCCTTGAGA CAATTCGACG TCCTGGTGAT   300

GCCAACGCTG CCCTACGTCG CATCCGAATT GCCGGCGAAG GACGTAGATC GTGCAACCTT   360
```

| | |
|---|---|
| CATCACCAAG GCTCTCGGGA TGATCGCCAA CACGGCACCA TTCGACGTGA CCGGACATCC | 420 |
| GTCCCTGTCC GTTCCGGCCG GCCTGGTGAA CGGGGTTCCG GTCGGAATGA TGATCACCGG | 480 |
| CAGACACTTC GACGATGCGA CAGTCCTTCG TGTCGGACGC GCATTCGAAA AGCTTCGCGG | 540 |
| CCGGTTTCCG ACGCCGGCCG AACGCGCCTC CAACTCTGCA CCACAACTCA GCCCCGCCTA | 600 |
| GTCCTGACGC ACTGTCAGAC AACAAATTCC ACCGATTCAC ACATGATCAG CCCACATAAG | 660 |

```
AAAAGGTGAA CCAG ATG TCA GTA ACG ATC GAC CAC ACA ACG GAG AAC GCC        710
              Met Ser Val Thr Ile Asp His Thr Thr Glu Asn Ala
               1               5                       10

GCA CCG GCC CAG GCG GCG GTC TCC GAC CGG GCG TGG GCA CTG TTC CGC        758
Ala Pro Ala Gln Ala Ala Val Ser Asp Arg Ala Trp Ala Leu Phe Arg
             15                  20                  25

GCA CTC GAC GGT AAG GGA TTG GTA CCC GAC GGT TAC GTC GAG GGA TGG        806
Ala Leu Asp Gly Lys Gly Leu Val Pro Asp Gly Tyr Val Glu Gly Trp
         30                  35                  40

AAG AAG ACC TCC GAG GAG GAC TTC AGT CCA AGG CGC GGA GCG GAA TTG        854
Lys Lys Thr Ser Glu Glu Asp Phe Ser Pro Arg Arg Gly Ala Glu Leu
 45                  50                  55                  60

GTA GCG CGC GCA TGG ACC GAC CCC GAG TTC CGG CAG CTG CTT CTC ACC        902
Val Ala Arg Ala Trp Thr Asp Pro Glu Phe Arg Gln Leu Leu Leu Thr
                 65                  70                  75

GAC GGT ACC GCC GCA GTT GCC CAG TAC GGA TAC CTG GGC CCC CAG GCG        950
Asp Gly Thr Ala Ala Val Ala Gln Tyr Gly Tyr Leu Gly Pro Gln Ala
             80                  85                  90

GCC TAC ATC GTG GCA GTC GAA GAC ACC CCG ACA CTC AAG AAC GTG ATC        998
Ala Tyr Ile Val Ala Val Glu Asp Thr Pro Thr Leu Lys Asn Val Ile
         95                  100                 105

GTG TGC TCG CTG TGT TCA TGC ACC GCG TGG CCC ATC CTC GGT CTG CCA       1046
Val Cys Ser Leu Cys Ser Cys Thr Ala Trp Pro Ile Leu Gly Leu Pro
 110                 115                 120

CCC ACC TGG TAC AAG AGC TTC GAA TAC CGT GCG CGC GTG GTC CGC GAA       1094
Pro Thr Trp Tyr Lys Ser Phe Glu Tyr Arg Ala Arg Val Val Arg Glu
125                 130                 135                 140

CCA CGG AAG GTT CTC TCC GAG ATG GGA ACC GAG ATC GCG TCG GAC ATC       1142
Pro Arg Lys Val Leu Ser Glu Met Gly Thr Glu Ile Ala Ser Asp Ile
                145                 150                 155

GAG ATT CGC GTC TAC GAC ACC ACC GCC GAA ACT CGC TAC ATG GTC CTC       1190
Glu Ile Arg Val Tyr Asp Thr Thr Ala Glu Thr Arg Tyr Met Val Leu
             160                 165                 170

CCG CAG CGT CCC GCC GGC ACC GAA GGC TGG AGC CAG GAA CAA CTG CAG       1238
Pro Gln Arg Pro Ala Gly Thr Glu Gly Trp Ser Gln Glu Gln Leu Gln
         175                 180                 185

GAA ATC GTC ACC AAG GAC TGC CTG ATC GGG GTT GCA ATC CCG CAG GTT       1286
Glu Ile Val Thr Lys Asp Cys Leu Ile Gly Val Ala Ile Pro Gln Val
 190                 195                 200

CCC ACC GTC TGATCACCCC GACAAGAAGG AAGCACACC ATG GAT GGA GTA CAC       1339
Pro Thr Val                                 Met Asp Gly Val His
205                                          1               5

GAT CTT GCC GGA GTA CAA GGC TTC GGC AAA GTC CCG CAT ACC GTC AAC       1387
Asp Leu Ala Gly Val Gln Gly Phe Gly Lys Val Pro His Thr Val Asn
             10                  15                  20

GCC GAC ATC GGC CCC ACC TTT CAC GCC GAA TGG GAA CAC CTG CCC TAC       1435
Ala Asp Ile Gly Pro Thr Phe His Ala Glu Trp Glu His Leu Pro Tyr
         25                  30                  35

AGC CTG ATG TTC GCC GGT GTC GCC GAA CTC GGG GCC TTC AGC GTC GAC       1483
Ser Leu Met Phe Ala Gly Val Ala Glu Leu Gly Ala Phe Ser Val Asp
             40                  45                  50

GAA GTG CGA TAC GTC GTC GAG CGG ATG GAG CCG GGC CAC TAC ATG ATG       1531
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Glu | Val | Arg | Tyr | Val | Val | Glu | Arg | Met | Glu | Pro | Gly | His | Tyr | Met | Met |      |
|     | 55  |     |     |     |     | 60  |     |     |     | 65  |     |     |     |     |     |      |
| ACC | CCG | TAC | TAC | GAG | AGG | TAC | GTC | ATC | GGT | GTC | GCG | ACA | TTG | ATG | GTC | 1579 |
| Thr | Pro | Tyr | Tyr | Glu | Arg | Tyr | Val | Ile | Gly | Val | Ala | Thr | Leu | Met | Val |      |
| 70  |     |     |     |     | 75  |     |     |     |     | 80  |     |     |     |     | 85  |      |
| GAA | AAG | GGA | ATC | CTG | ACG | CAG | GAC | GAA | CTC | GAA | AGC | CTT | GCG | GGG | GGA | 1627 |
| Glu | Lys | Gly | Ile | Leu | Thr | Gln | Asp | Glu | Leu | Glu | Ser | Leu | Ala | Gly | Gly |      |
|     |     |     |     |     | 90  |     |     |     |     | 95  |     |     |     |     | 100 |      |
| CCG | TTC | CCA | CTG | TCA | CGG | CCC | AGC | GAA | TCC | GAA | GGG | CGG | CCG | GCA | CCC | 1675 |
| Pro | Phe | Pro | Leu | Ser | Arg | Pro | Ser | Glu | Ser | Glu | Gly | Arg | Pro | Ala | Pro |      |
|     |     |     |     | 105 |     |     |     |     | 110 |     |     |     |     | 115 |     |      |
| GTC | GAG | ACG | ACC | ACC | TTC | GAA | GTC | GGG | CAG | CGA | GTA | CGC | GTA | CGC | GAC | 1723 |
| Val | Glu | Thr | Thr | Thr | Phe | Glu | Val | Gly | Gln | Arg | Val | Arg | Val | Arg | Asp |      |
|     |     | 120 |     |     |     |     | 125 |     |     |     |     | 130 |     |     |     |      |
| GAG | TAC | GTT | CCG | GGG | CAT | ATT | CGA | ATG | CCT | GCA | TAC | TGC | CGT | GGA | CGA | 1771 |
| Glu | Tyr | Val | Pro | Gly | His | Ile | Arg | Met | Pro | Ala | Tyr | Cys | Arg | Gly | Arg |      |
|     | 135 |     |     |     |     | 140 |     |     |     |     | 145 |     |     |     |     |      |
| GTG | GGA | ACC | ATC | TCT | CAT | CGA | ACT | ACC | GAG | AAG | TGG | CCG | TTT | CCC | GAC | 1819 |
| Val | Gly | Thr | Ile | Ser | His | Arg | Thr | Thr | Glu | Lys | Trp | Pro | Phe | Pro | Asp |      |
| 150 |     |     |     |     | 155 |     |     |     |     | 160 |     |     |     |     | 165 |      |
| GCA | ATC | GGC | CAC | GGG | CGC | AAC | GAC | GCC | GGC | GAA | GAA | CCG | ACG | TAC | CAC | 1867 |
| Ala | Ile | Gly | His | Gly | Arg | Asn | Asp | Ala | Gly | Glu | Glu | Pro | Thr | Tyr | His |      |
|     |     |     |     | 170 |     |     |     |     | 175 |     |     |     |     | 180 |     |      |
| GTG | AAG | TTC | GCC | GCC | GAG | GAA | TTG | TTC | GGT | AGC | GAC | ACC | GAC | GGT | GGA | 1915 |
| Val | Lys | Phe | Ala | Ala | Glu | Glu | Leu | Phe | Gly | Ser | Asp | Thr | Asp | Gly | Gly |      |
|     |     |     |     | 185 |     |     |     |     | 190 |     |     |     |     | 195 |     |      |
| AGC | GTC | GTT | GTC | GAC | CTC | TTC | GAG | GGT | TAC | CTC | GAG | CCT | GCG | GCC |     | 1960 |
| Ser | Val | Val | Val | Asp | Leu | Phe | Glu | Gly | Tyr | Leu | Glu | Pro | Ala | Ala |     |      |
|     | 200 |     |     |     |     | 205 |     |     |     |     | 210 |     |     |     |     |      |

```
TGATCTTCCA GCATTCCAGG CGGCGGTCAC GCGATCACAG CGGTTCGTGC GACCGCCGCC    2020

TGATCACCAC GATTCACTCA TTCGGAAGGA CACTGGAAAT CATGGTCGAC                2070
```

( 2 ) INFORMATION FOR SEQ ID NO:14:

( i ) SEQUENCE CHARACTERISTICS:
        ( A ) LENGTH: 1970 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Rhodococcus rhodochrous
        ( B ) STRAIN: J-1 (FERM BP-1478)

( i x ) FEATURE:
        ( A ) NAME/KEY: CDS
        ( B ) LOCATION: 408..1094

( i x ) FEATURE:
        ( A ) NAME/KEY: CDS
        ( B ) LOCATION: 1111..1719

( x i ) SEQUENCE DESCRIPTION: SEQ ID NO:14:

```
CTGCAGCTCG AACATCGAAG GGTGCGAGCC GAGAGATCGG AGACGCAGAC ACCCGGAGGG     60

AACTTAGCCT CCCGGACCGA TGCGTGTCCT GGCAACGCCT CAAAATTCAG TGCAAGCGAT    120

TCAATCTTGT TACTTCCAGA ACCGAATCAC GTCCCCGTAG TGTGCGGGGA GAGCGCCCGA    180

ACGCAGGGAT GGTATCCATG CGCCCCTTCT CTTTTCGAAC GAGAACCGGC CGGTACAGCC    240

GACCCGGAGA CACTGTGACG CCGTTCAACG ATTGTTGTGC TGTGAAGGAT TCACCCAAGC    300

CAACTGATAT CGCCATTCCG TTGCCGGAAC ATTTGACACC TTCTCCCTAC GAGTAGAAGC    360
```

```
CAGCTGGACC CCTCTTTGAG CCCAGCTCCG ATGAAAGGAA TGAGGAA ATG GAT GGT                      416
                                                       Met Asp Gly
                                                         1

ATC CAC GAC ACA GGC GGC ATG ACC GGA TAC GGA CCG GTC CCC TAT CAG                      464
Ile His Asp Thr Gly Gly Met Thr Gly Tyr Gly Pro Val Pro Tyr Gln
      5              10                  15

AAG GAC GAG CCC TTC TTC CAC TAC GAG TGG GAG GGT CGG ACC CTG TCA                      512
Lys Asp Glu Pro Phe Phe His Tyr Glu Trp Glu Gly Arg Thr Leu Ser
 20              25                  30                       35

ATT CTG ACT TGG ATG CAT CTC AAG GGC ATA TCG TGG TGG GAC AAG TCG                      560
Ile Leu Thr Trp Met His Leu Lys Gly Ile Ser Trp Trp Asp Lys Ser
             40                  45                  50

CGG TTC TTC CGG GAG TCG ATG GGG AAC GAA AAC TAC GTC AAC GAG ATT                      608
Arg Phe Phe Arg Glu Ser Met Gly Asn Glu Asn Tyr Val Asn Glu Ile
             55                  60                  65

CGC AAC TCG TAC TAC ACC CAC TGG CTG AGT GCG GCA GAA CGT ATC CTC                      656
Arg Asn Ser Tyr Tyr Thr His Trp Leu Ser Ala Ala Glu Arg Ile Leu
         70                  75                  80

GTC GCC GAC AAG ATC ATC ACC GAA GAA GAG CGA AAG CAC CGT GTG CAA                      704
Val Ala Asp Lys Ile Ile Thr Glu Glu Glu Arg Lys His Arg Val Gln
         85              90                  95

GAG ATC CTT GAG GGT CGG TAC ACG GAC AGG AAG CCG TCG CGG AAG TTC                      752
Glu Ile Leu Glu Gly Arg Tyr Thr Asp Arg Lys Pro Ser Arg Lys Phe
100              105                 110                     115

GAT CCG GCC CAG ATC GAG AAG GCG ATC GAA CGG CTT CAC GAG CCC CAC                      800
Asp Pro Ala Gln Ile Glu Lys Ala Ile Glu Arg Leu His Glu Pro His
             120                 125                 130

TCC CTA GCG CTT CCA GGA GCG GAG CCG AGT TTC TCT CTC GGT GAC AAG                      848
Ser Leu Ala Leu Pro Gly Ala Glu Pro Ser Phe Ser Leu Gly Asp Lys
         135                 140                 145

ATC AAA GTG AAG AGT ATG AAC CCG CTG GGA CAC ACA CGG TGC CCG AAA                      896
Ile Lys Val Lys Ser Met Asn Pro Leu Gly His Thr Arg Cys Pro Lys
         150                 155                 160

TAT GTG CGG AAC AAG ATC GGG GAA ATC GTC GCC TAC CAC GGC TGC CAG                      944
Tyr Val Arg Asn Lys Ile Gly Glu Ile Val Ala Tyr His Gly Cys Gln
    165                 170                 175

ATC TAT CCC GAG AGC AGC TCC GCC GGC CTC GGC GAC GAT CCT CGC CCG                      992
Ile Tyr Pro Glu Ser Ser Ser Ala Gly Leu Gly Asp Asp Pro Arg Pro
180             185                 190                 195

CTC TAC ACG GTC GCG TTT TCC GCC CAG GAA CTG TGG GGC GAC GAC GGA                     1040
Leu Tyr Thr Val Ala Phe Ser Ala Gln Glu Leu Trp Gly Asp Asp Gly
             200                 205                 210

AAC GGG AAA GAC GTA GTG TGC GTC GAT CTC TGG GAA CCG TAC CTG ATC                     1088
Asn Gly Lys Asp Val Val Cys Val Asp Leu Trp Glu Pro Tyr Leu Ile
         215                 220                 225

TCT GCG TGAAAGGAAT ACGATA GTG AGC GAG CAC GTC AAT AAG TAC ACG                       1137
Ser Ala                   Met Ser Glu His Val Asn Lys Tyr Thr
                            1               5

GAG TAC GAG GCA CGT ACC AAG GCG ATC GAA ACC TTG CTG TAC GAG CGA                     1185
Glu Tyr Glu Ala Arg Thr Lys Ala Ile Glu Thr Leu Leu Tyr Glu Arg
 10              15                  20                       25

GGG CTC ATC ACG CCC GCC GCG GTC GAC CGA GTC GTT TCG TAC TAC GAG                     1233
Gly Leu Ile Thr Pro Ala Ala Val Asp Arg Val Val Ser Tyr Tyr Glu
             30                  35                  40

AAC GAG ATC GGC CCG ATG GGC GGT GCC AAG GTC GTG GCC AAG TCC TGG                     1281
Asn Glu Ile Gly Pro Met Gly Gly Ala Lys Val Val Ala Lys Ser Trp
         45                  50                  55

GTG GAC CCT GAG TAC CGC AAG TGG CTC GAA GAG GAC GCG ACG GCC GCG                     1329
Val Asp Pro Glu Tyr Arg Lys Trp Leu Glu Glu Asp Ala Thr Ala Ala
         60                  65                  70
```

```
ATG GCG TCA TTG GGC TAT GCC GGT GAG CAG GCA CAC CAA ATT TCG GCG    1377
Met Ala Ser Leu Gly Tyr Ala Gly Glu Gln Ala His Gln Ile Ser Ala
    75                  80                  85

GTC TTC AAC GAC TCC CAA ACG CAT CAC GTG GTG GTG TGC ACT CTG TGT    1425
Val Phe Asn Asp Ser Gln Thr His His Val Val Val Cys Thr Leu Cys
 90                  95                 100                 105

TCG TGC TAT CCG TGG CCG GTG CTT GGT CTC CCG CCC GCC TGG TAC AAG    1473
Ser Cys Tyr Pro Trp Pro Val Leu Gly Leu Pro Pro Ala Trp Tyr Lys
                    110                 115                 120

AGC ATG GAG TAC CGG TCC CGA GTG GTA GCG GAC CCT CGT GGA GTG CTC    1521
Ser Met Glu Tyr Arg Ser Arg Val Val Ala Asp Pro Arg Gly Val Leu
            125                 130                 135

AAG CGC GAT TTC GGT TTC GAC ATC CCC GAT GAG GTG GAG GTC AGG GTT    1569
Lys Arg Asp Phe Gly Phe Asp Ile Pro Asp Glu Val Glu Val Arg Val
        140                 145                 150

TGG GAC AGC AGC TCC GAA ATC CGC TAC ATC GTC ATC CCG GAA CGG CCG    1617
Trp Asp Ser Ser Ser Glu Ile Arg Tyr Ile Val Ile Pro Glu Arg Pro
    155                 160                 165

GCC GGC ACC GAC GGT TGG TCC GAG GAG GAG CTG ACG AAG CTG GTG AGC    1665
Ala Gly Thr Asp Gly Trp Ser Glu Glu Glu Leu Thr Lys Leu Val Ser
170                 175                 180                 185

CGG GAC TCG ATG ATC GGT GTC AGT AAT GCG CTC ACA CCG CAG GAA GTG    1713
Arg Asp Ser Met Ile Gly Val Ser Asn Ala Leu Thr Pro Gln Glu Val
                190                 195                 200

ATC GTA TGAGTGAAGA CACACTCACT GATCGGCTCC CGGCGACTGG GACCGCCGCA    1769
Ile Val
CCGCCCCGCG ACAATGGCGA GCTTGTATTC ACCGAGCCTT GGGAAGCAAC GGCATTCGGG    1829
GTCGCCATCG CGCTTTCGGA TCAGAAGTCG TACGAATGGG AGTTCTTCCG ACAGCGTCTC    1889
ATTCACTCCA TCGCTGAGGC CAACGGTTGC GAGGCATACT ACGAGAGCTG GACAAAGGCG    1949
CTCGAGGCCA GCGTGGTCGA C                                            1970
```

( 2 ) INFORMATION FOR SEQ ID NO:15:

( i ) SEQUENCE CHARACTERISTICS:
        ( A ) LENGTH: 1731 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Rhodococcus rhodochrous
        ( B ) STRAIN: J-1 (FERM BP-1478)

( i x ) FEATURE:
        ( A ) NAME/KEY: CDS
        ( B ) LOCATION: 171..848

( i x ) FEATURE:
        ( A ) NAME/KEY: CDS
        ( B ) LOCATION: 915..1535

( x i ) SEQUENCE DESCRIPTION: SEQ ID NO:15:

```
GAGCTCCCTG GAGCCACTCG CGCCGACGCA TCCACGCTCG GACAGCCCAC GGTGCGGATC    60

ACCCCTGTTC GTCGGTAACA GAACAGTAAC ATGTCATCAG GTCATGACGT GTTGACGCAT   120

TAGACGAGGG CACATAGGGT TGGTGACTCA CGGCACAAGG AGAGCATTTC ATG GAT      176
                                                      Met Asp
                                                        1

GGA ATC CAC GAC CTC GGT GGC CGC GCC GGC CTG GGT CCG ATC AAG CCC    224
Gly Ile His Asp Leu Gly Gly Arg Ala Gly Leu Gly Pro Ile Lys Pro
      5                  10                  15

GAA TCC GAT GAA CCT GTT TTC CAT TCC GAT TGG GAG CGG TCG GTT TTG    272
```

| | | | | | | | | | | | | | | | | |
|---|---|---|---|---|---|---|---|---|---|---|---|---|---|---|---|---|
| Glu | Ser | Asp | Glu | Pro | Val | Phe | His | Ser | Asp | Trp | Glu | Arg | Ser | Val | Leu | |
| | 20 | | | | 25 | | | | | 30 | | | | | | |
| ACG | ATG | TTC | CCG | GCG | ATG | GCG | CTG | GCC | GGC | GCG | TTC | AAT | CTC | GAC | CAG | 320 |
| Thr | Met | Phe | Pro | Ala | Met | Ala | Leu | Ala | Gly | Ala | Phe | Asn | Leu | Asp | Gln | |
| 35 | | | | | 40 | | | | | 45 | | | | | 50 | |
| TTC | CGG | GGC | GCG | ATG | GAG | CAG | ATC | CCC | CCG | CAC | GAC | TAC | CTG | ACC | TCG | 368 |
| Phe | Arg | Gly | Ala | Met | Glu | Gln | Ile | Pro | Pro | His | Asp | Tyr | Leu | Thr | Ser | |
| | | | | 55 | | | | | 60 | | | | | 65 | | |
| CAA | TAC | TAC | GAG | CAC | TGG | ATG | CAC | GCG | ATG | ATC | CAC | CAC | GGC | ATC | GAG | 416 |
| Gln | Tyr | Tyr | Glu | His | Trp | Met | His | Ala | Met | Ile | His | His | Gly | Ile | Glu | |
| | | | 70 | | | | 75 | | | | | 80 | | | | |
| GCG | GGC | ATC | TTC | GAT | TCC | GAC | GAA | CTC | GAC | CGC | CGC | ACC | CAG | TAC | TAC | 464 |
| Ala | Gly | Ile | Phe | Asp | Ser | Asp | Glu | Leu | Asp | Arg | Arg | Thr | Gln | Tyr | Tyr | |
| | | 85 | | | | | 90 | | | | | 95 | | | | |
| ATG | GAC | CAT | CCG | GAC | GAC | ACG | ACC | CCC | ACG | CGG | CAG | GAT | CCG | CAA | CTG | 512 |
| Met | Asp | His | Pro | Asp | Asp | Thr | Thr | Pro | Thr | Arg | Gln | Asp | Pro | Gln | Leu | |
| | | 100 | | | | | 105 | | | | | 110 | | | | |
| GTG | GAG | ACG | ATC | TCG | CAA | CTG | ATC | ACC | CAC | GGA | GCC | GAT | TAC | CGA | CGC | 560 |
| Val | Glu | Thr | Ile | Ser | Gln | Leu | Ile | Thr | His | Gly | Ala | Asp | Tyr | Arg | Arg | |
| 115 | | | | | 120 | | | | | 125 | | | | | 130 | |
| CCG | ACC | GAC | ACC | GAG | GCC | GCA | TTC | GCC | GTA | GGC | GAC | AAA | GTC | ATC | GTG | 608 |
| Pro | Thr | Asp | Thr | Glu | Ala | Ala | Phe | Ala | Val | Gly | Asp | Lys | Val | Ile | Val | |
| | | | | 135 | | | | | 140 | | | | | 145 | | |
| CGG | TCG | GAC | GCC | TCA | CCG | AAC | ACC | CAC | ACC | CGC | CGC | GCC | GGA | TAC | GTC | 656 |
| Arg | Ser | Asp | Ala | Ser | Pro | Asn | Thr | His | Thr | Arg | Arg | Ala | Gly | Tyr | Val | |
| | | | | 150 | | | | | 155 | | | | | 160 | | |
| CGC | GGT | CGT | GTC | GGC | GAA | GTC | GTG | GCG | ACC | CAC | GGC | GCG | TAT | GTC | TTT | 704 |
| Arg | Gly | Arg | Val | Gly | Glu | Val | Val | Ala | Thr | His | Gly | Ala | Tyr | Val | Phe | |
| | | 165 | | | | | 170 | | | | | 175 | | | | |
| CCG | GAC | ACC | AAC | GCA | CTC | GGC | GCC | GGC | GAA | AGC | CCC | GAA | CAC | CTG | TAC | 752 |
| Pro | Asp | Thr | Asn | Ala | Leu | Gly | Ala | Gly | Glu | Ser | Pro | Glu | His | Leu | Tyr | |
| | | 180 | | | | | 185 | | | | | 190 | | | | |
| ACC | GTG | CGG | TTC | TCG | GCG | ACC | GAG | TTG | TGG | GGT | GAA | CCT | GCC | GCC | CCG | 800 |
| Thr | Val | Arg | Phe | Ser | Ala | Thr | Glu | Leu | Trp | Gly | Glu | Pro | Ala | Ala | Pro | |
| 195 | | | | | 200 | | | | | 205 | | | | | 210 | |
| AAC | GTC | GTC | AAT | CAC | ATC | GAC | GTG | TTC | GAA | CCG | TAT | CTG | CTA | CCG | GCC | 848 |
| Asn | Val | Val | Asn | His | Ile | Asp | Val | Phe | Glu | Pro | Tyr | Leu | Leu | Pro | Ala | |
| | | | | 215 | | | | | 220 | | | | | 225 | | |
| TGACCAGGTC | ATCCGGTCCA | CCCAGCGAGA | CGTCCCTTCA | CCACAGACAG | AAACGAGCCC | | | | | | | | | | | 908 |
| ACCCCG | ATG | ACC | GCC | CAC | AAT | CCC | GTC | CAG | GGC | ACG | TTG | CCA | CGA | TCG | | 956 |
| | Met | Thr | Ala | His | Asn | Pro | Val | Gln | Gly | Thr | Leu | Pro | Arg | Ser | | |
| | 1 | | | | 5 | | | | | 10 | | | | | | |
| AAC | GAG | GAG | ATC | GCC | GCA | CGC | GTG | AAG | GCC | ATG | GAG | GCC | ATC | CTC | GTC | 1004 |
| Asn | Glu | Glu | Ile | Ala | Ala | Arg | Val | Lys | Ala | Met | Glu | Ala | Ile | Leu | Val | |
| 15 | | | | | 20 | | | | | 25 | | | | | 30 | |
| GAC | AAG | GGC | CTG | ATC | TCC | ACC | GAC | GCC | ATC | GAC | CAC | ATG | TCC | TCG | GTC | 1052 |
| Asp | Lys | Gly | Leu | Ile | Ser | Thr | Asp | Ala | Ile | Asp | His | Met | Ser | Ser | Val | |
| | | | | 35 | | | | | 40 | | | | | 45 | | |
| TAC | GAG | AAC | GAG | GTC | GGT | CCT | CAA | CTC | GGC | GCC | AAG | ATC | GTC | GCC | CGC | 1100 |
| Tyr | Glu | Asn | Glu | Val | Gly | Pro | Gln | Leu | Gly | Ala | Lys | Ile | Val | Ala | Arg | |
| | | | 50 | | | | 55 | | | | | 60 | | | | |
| GCC | TGG | GTC | GAT | CCC | GAG | TTC | AAG | CAG | CGC | CTG | CTC | ACC | GAC | GCC | ACC | 1148 |
| Ala | Trp | Val | Asp | Pro | Glu | Phe | Lys | Gln | Arg | Leu | Leu | Thr | Asp | Ala | Thr | |
| | | 65 | | | | | 70 | | | | | 75 | | | | |
| AGC | GCC | TGC | CGT | GAA | ATG | GGC | GTC | GGC | GGC | ATG | CAG | GGC | GAA | GAA | ATG | 1196 |
| Ser | Ala | Cys | Arg | Glu | Met | Gly | Val | Gly | Gly | Met | Gln | Gly | Glu | Glu | Met | |
| | 80 | | | | | 85 | | | | | 90 | | | | | |
| GTC | GTG | CTG | GAA | AAC | ACC | GGC | ACG | GTC | CAC | AAC | ATG | GTC | GTA | TGT | ACC | 1244 |
| Val | Val | Leu | Glu | Asn | Thr | Gly | Thr | Val | His | Asn | Met | Val | Val | Cys | Thr | |
| 95 | | | | | 100 | | | | | 105 | | | | | 110 | |

```
TTG  TGC  TCG  TGC  TAT  CCG  TGG  CCG  GTT  CTC  GGC  CTG  CCA  CCC  AAC  TGG    1292
Leu  Cys  Ser  Cys  Tyr  Pro  Trp  Pro  Val  Leu  Gly  Leu  Pro  Pro  Asn  Trp
               115                      120                      125

TAC  AAG  TAC  CCC  GCC  TAC  CGC  GCC  CGC  GCT  GTC  CGC  GAC  CCC  CGA  GGT    1340
Tyr  Lys  Tyr  Pro  Ala  Tyr  Arg  Ala  Arg  Ala  Val  Arg  Asp  Pro  Arg  Gly
               130                      135                      140

GTG  CTG  GCC  GAA  TTC  GGA  TAT  ACC  CCC  GAC  CCT  GAC  GTC  GAG  ATC  CGG    1388
Val  Leu  Ala  Glu  Phe  Gly  Tyr  Thr  Pro  Asp  Pro  Asp  Val  Glu  Ile  Arg
          145                      150                      155

ATA  TGG  GAC  TCG  AGT  GCC  GAA  CTT  CGC  TAC  TGG  GTC  CTG  CCG  CAA  CGC    1436
Ile  Trp  Asp  Ser  Ser  Ala  Glu  Leu  Arg  Tyr  Trp  Val  Leu  Pro  Gln  Arg
     160                      165                      170

CCA  GCC  GGC  ACC  GAG  AAC  TTC  ACC  GAA  GAA  CAA  CTC  GCC  GAC  CTC  GTC    1484
Pro  Ala  Gly  Thr  Glu  Asn  Phe  Thr  Glu  Glu  Gln  Leu  Ala  Asp  Leu  Val
175                      180                      185                      190

ACC  CGC  GAC  TCG  CTC  ATC  GGC  GTA  TCC  GTC  CCC  ACC  ACA  CCC  AGC  AAG    1532
Thr  Arg  Asp  Ser  Leu  Ile  Gly  Val  Ser  Val  Pro  Thr  Thr  Pro  Ser  Lys
               195                      200                      205

GCC  TGACATGCCC  CGACTCAACG  AACAACCCCA  CCCGGGTCTC  GAAGCCAACC                   1585
Ala

TCGGCGACCT  GGTACAGAAT  CTGCCGTTCA  ACGAACGAAT  CCCCCGCCGC  TCCGGCGAGG            1645

TCGCCTTCGA  TCAGGCCTGG  GAGATCCGCG  CCTTCAGCAT  TGCCACCGCA  TTGCATGGCC            1705

AGGGCCGATT  CGAATGGGAC  GAATTC                                                   1731
```

DNA FRAGMENT ENCODING A POLYPEPTIDE HAVING NITRILE HYDRATASE ACTIVITY, A TRANSFORMANT CONTAINING THE GENE AND A PROCESS FOR THE PRODUCTION OF AMIDES USING THE TRANSFORMANT

This is a continuation of application Ser. No. 07/697,747, filed May 2, 1991, abandoned.

FIELD OF THE INVENTION

The present invention relates to a DNA fragment derived from *Rhodococcus rhodochrous* J-1 and encoding a polypeptide having nitrile hydratase activity which hydrates nitriles to amides. The invention also relates to a recombinant DNA containing the above DNA fragment, and a transformant transformed with the recombinant DNA. The present invention further relates to a method of producing nitrile hydratase using the transformant and of amides using nitrile hydratase.

PRIOR ART

Nitrile hydratase or nitrilase is known as an enzyme that hydrates nitriles to amides. Microorganisms that produce nitrile hydratase include those belonging to the genus Bacillus, the genus Bacteridium, the genus Micrococcus and the genus Brevibacterium (See, JP-B-62-21517/1989, U.S. Pat. No. 4,001,081), the genus Corynebacterium and the genus Nocardia (See, JP-B-56-17918/1981, U.S. Pat. No. 4,248,968), the genus Pseudomonas (See, JP-B-59-37951/1984, U.S. Pat. No. 4,637,982), the genus Rhodococcus, the genus Arthrobacter and the genus Microbacterium (See, JP-A-61-162193/1986, EP-A-0188316), and *Rhodococcus rhodochrous* (See, JP-A-2-470/1990, EP-A-0307926).

Nitrile hydratase has been used to hydrate nitriles to amides. In the invention, microorganisms are engineered to contain multiple copies of a recombinant DNA encoding nitrile hydratase according to a recombinant DNA technology. The recombinant produces a remarkably high level of nitrile hydratase compared with conventionally used microorganisms.

The present inventors previously disclosed a DNA fragment derived from Rhodococcus sp. N-774 (FERM BP-1936) which also encodes a polypeptide having nitrile hydratase activity (JP-A-2-119778/1988).

In contrast, the present inventors utilizes a DNA fragment derived from *Rhodococcus rhodochrous* J-1 for the production of nitrile hydratase. We isolated the gene encoding nitrile hydratase, inserted the gene into a suitable plasmid vector and transformed an appropriate host with the recombinant plasmid, thus successfully obtained the transformant producing nitrile hydratase which has high activity also on aromatic nitriles.

SUMMARY OF THE INVENTION

The present invention relates to
(1) a DNA$^{(H)}$ fragment encoding a polypeptide having nitrile hydratase activity, said polypeptide comprising $\alpha^{(H)}$-subunit as defined in the Sequence Listing by SEQ ID: No. 1 and $\beta^{(H)}$-subunit as defined in the Sequence Listing by SEQ ID: No. 2.
(2) A DNA$^{(L)}$ fragment encoding a polypeptide having nitrile hydratase activity, said polypeptide comprising $\alpha^{(L)}$-subunit as defined in the Sequence Listing by SEQ ID: No. 3 and $\beta^{(L)}$-subunit as defined in the Sequence Listing by SEQ ID: No. 4.
(3) the DNA$^{(H)}$ fragment of (1) which contrives a nucleotide sequence encoding said $\alpha^{(H)}$- and $\beta^{(H)}$-subunits, comprising: DNA sequence of $\alpha^{(H)}$-subunit as defined in the Sequence Listing by SEQ ID: No. 5 and DNA sequence of $\beta^{(H)}$-subunit as defined in the Sequence Listing by SEQ ID: No. 6.
(4) the DNA$^{(L)}$ fragment of (2) which contains a nucleotide sequence encoding said $\alpha^{(L)}$- and $\beta^{(L)}$-subunits, comprising: DNA sequence of $\alpha^{(L)}$-subunit as defined in the Sequence Listing by SEQ ID: No. 7 and DNA sequence of $\beta^{(L)}$-subunit as defined in the Sequence Listing by SEQ ID: No. 8.
(5) a recombinant DNA comprising the DNA$^{(H)}$ or the DNA$^{(L)}$ of (1)–(4) in a vector; and
(6) a transformant transformed with the recombinant DNA of (5).
(7) a method for the production of nitrile hydratase which comprises culturing the transformant as described in (6) and recovering nitrile hydratase from the culture;
(8) a method for the production of amides which comprises hydrating nitriles using nitrile hydratase as described in (7) to form amides; and
(9) a method for the production of amides which comprises culturing the transformant as described in (6), and hydrating nitriles using the resultant culture isolated bacterial cells, treated matter thereof, or a fixed material of them, to form amides.

The present invention is described in detail as follows.

The present invention is carried out by the steps (1)–(8):

(1) Isolation and Purification of Nitrile Hydratase and Partial Amino Acid Sequencing of Nitrile Hydratase Two types of nitrile hydratase (designated as H type and L type, respectively) are isolated and purified from *Rhodococcus rhodochrous* J-1 (FERM BP-1478) and the both enzymes are separated into $\alpha$ and $\beta$ subunits using HPLC. N-Terminal amino acid sequence each of the subunits is determined and shown in the Sequence Listing by SEQ ID: Nos. 9–12.

(2) Preparation of a DNA Probe for a Nitrile Hydratase Gene

A DNA probe is prepared from JM105/pYUK121 (FERM BP-1937) as described in JP-A-2-119778/1990 due to the high degree of homology in the amino acid sequence between the nitrile hydratase $\beta$ subunit of Rhodococcus sp. N-774 described in said Japanese Patent Official Gazette and those of *Rhodococcus rhodochrous* J-1. Plasmid pYUK121 containing nitrile hydratase gene derived from Rhodococcus sp. N-774 is prepared from a JM105/pYUK121 culture. pYUK121 DNA is digested with SphI and SalI. The SphI-SalI fragment contains the nitrile hydratase gene (shown in the Sequence Listing by SEQ ID: No. 13) of Rhodococcus sp. N-774. The DNA fragment is radiolabeled.

(3) Detection of a DNA Segment Containing a Nitrile Hydratase Gene from the Chromosome of *Rhodococcus rhodochrous* J-1

Chromosomal DNA is prepared from a *Rhodococcus rhodochrous* J-1 culture. The chromosomal DNA is digested with restriction enzymes and hybridized to the probe described in (2) using a Southern hybridization method [Southern, E. M., J. Mol. Biol. 98, 503 (1975)].

Two DNA fragments of a different length are screened.

(4) Construction of a Recombinant Plasmid

A recombinant plasmid is constructed by inserting the chromosomal DNA fragment as prepared in (3) into a plasmid vector.

(5) Transformation and Screening of the Transformant Containing the Recombinant Plasmid Transformants are prepared using the recombinant plasmid as described in (4). The transformant containing the recombinant plasmid is selected using the probe as described in (2) according to a colony hybridization method [R. Bruce Wallace et. al., Nuc. Aci. Res. 9, 879 (1981)]. Additionally, the presence of the nitrile hydratase gene in the recombinant plasmid is confirmed using a Southern hybridization method. The plasmids thus selected are designated as pNHJ10H and pNHJ20L.

(6) Isolation and Purification of Plasmid DNA and Construction of the Restriction Map Plasmid DNAs of pNHJ10H and pNHJ20L as prepared in (5) are isolated and purified. The restriction map of the DNAs is constructed (FIG. 1) to determine the region containing nitrile hydratase gene.

(7) DNA Sequencing

The extra segment of the inserted DNA fragment in pNHJ10H and pNHJ20L is excised using an appropriate restriction enzyme. The inserted DNA fragment is then used for sequencing. The nucleotide sequence of the DNA fragment(SEQ: ID Nos. 14, 15) reveals that it contains the sequence deduced from the amino acid sequence as described in (1).

(8) Production of Nitrile Hydratase Using the Transformant and Conversion of Nitriles to Amides The transformant as described in (8) is cultured. The bacterial cells are mixed with nitriles, a substrate of nitrile hydratase, and amides are produced.

*Rhodococcus rhodochrous* J-1 was deposited with Fermentation Research Institute, Agency of Industrial Science and Technology, and was assigned the accession number FERM BP-1478. A transformant TG1/pNHJ10H containing pNHJ10H as described in (5) and a transformant TG1/pNHJ20L containing pNHJ20L as described in (5) were deposited with the above and assigned the accession number FERM BP-2777 and FERM BP-2778, respectively.

Any vectors including a plasmid vector (e.g., pAT153, pMP9, pHC624, pKC7, etc.), a phage vector (e.g., λgt11 (Toyobo), Charon 4A (Amersham), etc.)may be used. Enzymes which may be used include SphI, SalI, EcoRI, BamHI, SacI, and the like, which are commercially available (Takara Shuzo). Various hosts may be used for transformation including but not limited to *E. coli* JM105 and *E. coli* TG1.

Culture media for the transformant are those ordinarily used in the art.

Conversion of nitriles to amides is carried out using nitrile hydratase, crude nitrile hydratase, the culture of the transformant, the isolated bacterial cells or treated matter thereof, and the like, prepared from the culture of the transformant.

Suitable nitriles in the invention include aromatic nitriles having 4–10 carbon atoms in the aromatic moiety and aliphatic nitriles having 2–6 carbon atoms, which are described in the European Patent Publication No. 0,307,926. Typical examples of the nitriles are 4-, 3- and 2-cyanopyridines, benzonitrile, 2,6-difluorobenzonitrile, 2-thiophene carbonitrile, 2-furonitrile, cyanopyrazine, acrylonitrile, methacrylonitrile, crotonitrile, acetonitrile and 3-hydroxypropionitrile.

The Effect of the Invention

The present invention has disclosed the amino acid sequence and nucleotide sequence of the α- and β-subunits of two types of nitrile hydratase derived from *Rhodococcus rhodochrous* J-1. The DNA fragment encoding nitrile hydratase is inserted into an expression vector and the recombinant vector is used for transformation. The transformant contains multiple copies of the gene and can produce much higher level of nitrile hydratase compared with conventionally used microorganisms.

Description of the Figure

FIG. 1 shows restriction maps of recombinant plasmids, pNHJ10H and pNHJ20L.

The present invention will be illustrated in detail in the following Example which is not intended to limit the scope of the invention.

The following abbreviation is used in Example.
TE: Tris-HCl (10 mM; pH 7.8), EDTA (1 mM, pH 8.0)
TNE: Tris-HCl (50 mM; pH 8.0), EDTA (1 mM, pH 8.0), NaCl (50 mM)
STE: Tris-HCl (50 mM; pH 8.0), EDTA (5 mM, pH 8.0), Sucrose (35 mM)
2×YT medium: 1.6% Trypton; 1.0% Yeast extract, 0.5% NaCl

EXAMPLE (1) Isolation and Purification of Nitrile Hydratase and Partial Amino Acid Sequencing of Nitrile Hydratase

*Rhodococcus rhodochrous* J-1 was cultured in a medium (3 g/l of yeast extract, 0.5 g/l of $KH_2PO_4$, 0.5 g/l of $K_2HPO_4$, 0.5 g/l of $MgSO_4 \cdot 4H_2O$, 0.01 g/l of $CoCl_2$, and 3 g/l of crotonamide, pH 7.2) at 28° C. for 80 hours. The bacterial cells were harvested. 50 g of the bacterial cells was disrupted and fractionated with ammonium sulfate. The sample was dialyzed and the dialysate was centrifuged. The supernatant was loaded on DEAE-Cellulofine chromatography, Phenyl-Sepharose chromatography, Sephadex G-150 chromatography and Octyl-Sepharose chromatography. Two fractions with enzyme activity were obtained and dialyzed. The dialysates were loaded on a high performance liquid chromatography using a reversed phase column (Senshu Pak VP-304-1251, Senshu Kagaku), and two respective subunits (α and β) were obtained. N-terminal amino acid sequence of $\alpha_1^{(H)}$-, $\beta_1^{(H)}$0, $\alpha_1^{(L)}$- and $\beta_1^{(L)}$-subunits was determined using an Applied Biosystems model 470A protein sequencer. The amino acid sequences are shown in the Sequence Listing by SEQ ID: Nos. 9–12.

(2) Preparation of a DNA Probe for Nitrile Hydratase Gene

*E. coli* JM105 (FERM BP-1937) containing pYUK121 was cultured in 100 ml of 2×YT medium containing 50 µg/ml of ampicillin at 30° C. overnight (12 hours). The bacterial cells were harvested and TNE was added to the cells. The cell suspension was then centrifuged. 8 ml of STE and 10 mg of lysozyme were added to the pellet. The mixture was incubated at 0° C. for five minutes followed by the addition of 4 ml of 0.25M EDTA. 2 ml of 10% SDS and 5 ml of 5M NaCl were then added to the mixture at room temperature. The resultant mixture was incubated at 0°–4° C. for three hours and then ultracentrifuged. ½ volume of 30% PEG 6000 was added to the supernatant. The mixture was incubated at 0°–4° C. overnight (12 hours) and centrifuged. TNE was added to the pellet to bring the volume to 7.5 ml and CsCl was then added to the suspension. The mixture was centrifuged to remove proteins. Then, 300–500 mg/ml of ethidium bromide was added to the supernatant. The mixture was transferred to a centrifuge tube. The tube was heat-sealed and then ultracentrifuged. cccDNA was extracted using a peristaltic pump. A bit more than equal amount of isopropyl alcohol saturated with water was added to the extract to rid of ethidium bromide. The sample was dialyzed against TE. About 3 ml of purified pYUK121 was obtained.

pYUK121 DNA was digested with SphI and SalI, resulting in a 2.07 kb DNA fragment containing a nitrile hydratase gene derived from Rhodococcus sp. N-774. The fragment was radiolabeled with $^{32}P$ to produce a probe. The nucleotide sequence of the probe is shown in the Sequence Listing by SEQ ID: No. 13.

(3) Preparation of a DNA Fragment Containing a Nitrile Hydratase Gene of Chromosome

*Rhodococcus rhodochrous* J-1 was cultured in 100 ml of a medium (10 g/l of glucose, 0.5 g/l of $KH_2PO_4$, 0.5 g/l of $K_2HPO_4$, 0.5 g/l of $MgSO_4.7H_2O$, 1 g/l of yeast extract, 7.5 g/l of peptone, 0.01 g/l of $CoCl_2$, 7.5 g/l of urea, 1% glycine or 0.2 µg/ml of ampicillin, 1 l of water, pH 7.2). The bacterial cells were harvested and the pellet was washed with TNE. The pellet was then suspended in 10 ml of TE. 4 ml of 0.25M EDTA, 10–20 mg of lysozyme, 10–20 mg of achromoprotease and 10 ml of 10×SDS were added to the suspension. The suspension was incubated at 37° C. for three hours. 15 ml of phenol was added to the suspension. The mixture was incubated at room temperature for 15 minutes and then centrifuged. The upper layer was removed, and 0.7 ml of 2.5M sodium acetate and diethyl ether were added to the supernatant. The mixture was centrifuged and the upper layer war discarded. Two volumes of ethanol were added to the bottom layer and DNA was removed with a glass rod. DNA was rinsed for five minutes each with TE:ethanol 2:8, 1:9, and 0:10 (v/v). DNA was then resuspended in 2–4 ml of TE (37° C.). 10 µl of a mixture of RNase A and $T_1$ was added to the suspension and the mixture was incubated at 37° C. An equal amount of phenol was added to the mixture which was then centrifuged. More than equal amount of ether was added to the supernatant. The mixture was centrifuged again, and the upper layer was discarded and the bottom layer was saved. The bottom layer was dialyzed against 2 l of TE containing a small amount of chloroform overnight and further dialyzed against fresh TE for 3–4 hours. 4 ml of crude chromosomal DNA was obtained.

10 µl of TE, 3 µl reaction buffer (10×) and 2 µl of SacI were added to 15 µl of crude chromosomal DNA. The mixture was incubated at 37° C. for an hour and electrophoresed on an agarose gel at 60 V for three hours. The Southern hybridization of chromosomal DNA was carried out using the probe as described in (2). About 6.0 kb and 9.4 kb fragments were found to show a strong hybridization.

15 µl of chromosomal DNA was digested with SacI and electrophoresed on an agarose gel, as described above. 6.0 kb and 9.4 kb DNA fragments were cut out from the gel and taken in three volumes each of 8M $NaClO_4$. After solubilization, each solution was dotted on GF/C (Whatman) filter paper (6 mm in diameter). Ten drops ($\cong$100 µl) of TE containing 6M $NaClO_4$ and then ten drops ($\cong$100 µl) of 95% ethanol were added to the filter paper. The paper was air-dried for 3 minutes and placed in 0.5 ml Eppendorf tube. 40 µl of TE was added to the tube and the whole was incubated at 47° C. for 30 minutes. The tube was then centrifuged. About 40 µl of the supernatant was obtained which contained 6.0 kb and 9.4 kb DNA fragments containing a nitrile hydratase gene of chromosomal DNA.

The method of inserting the 6.0 kb DNA fragment into a vector is described below. The same method is applied for the insertion of the 9.4 kb DNA fragment into a vector.

(4) Insertion of the Chromosomal DNA Fragment into a Vector

10 µl of TE, 3 µl of reaction buffer (10×) and 2 µl of SacI was added to 10 µl of pUC19. The mixture was incubated at 30° C. for an hour. 2 µl of 0.25M EDTA was added to the mixture to stop the reaction. Then, 7 µl of 1M Tris-HCl (pH 9) and 3 µl of BAP (bacterial alkaline phosphatase) were added to the mixture. The mixture was incubated at 65° C. for an hour. TE was then added to the mixture to make a total volume to 100 µl. The mixture was extracted 3× with an equal amount of phenol. An equal amount of ether was added to the extract. The bottom layer was removed and 10 µl of 3M sodium acetate and 250 µl of ethanol were added to the bottom layer. The mixture was incubated at −80° C. for 30 minutes, centrifuged, dried, and resuspended in TE.

5 µl of pUC19 DNA thus obtained and 40 µl of the 6.0 kb DNA fragment as described in (3) were mixed. 6 µl of ligation buffer, 6 µl of ATP (6 mg/ml) and 3 µl of T4 DNA ligase were added to the mixture. The mixture was incubated at 4° C. overnight (12 hours) to produce the recombinant plasmid containing the 6.0 kb DNA fragment encoding the desired enzyme in the SacI site of pUC19.

(5) Transformation and Screening of Transformants

*E. coli* TG1 (Amersham) was inoculated into 10 ml of 2×YT medium and incubated at 37° C. for 12 hours. After incubation, the resultant culture was added to fresh 2×YT medium to a concentration of 1%, and the mixture was incubated at 37° C. for two hours. The culture was centrifuged and the pellet was suspended in 5 ml of cold 50 mM $CaCl_2$. The suspension was placed on ice for 40 minutes and then centrifuged. 0.25 ml of cold 50 mM $CaCl_2$ and 60 µl of the recombinant DNA as described in (4) were added to the pellet. The mixture was incubated at 0° C. for 40 minutes, heat-shocked at 42° C. for two minutes, placed on ice for five minutes, and added to 10 ml of 2×YT medium. The mixture was incubated at 37° C. for 90 minutes with shaking, then centrifuged. The pellet was suspended in 1 ml of 2×YT medium, and two 10 µl aliquots of the suspension were plated on a 2×YT agar plate containing 50 µg/ml of ampicillin separately. The plate was incubated at 37° C. The colony grown on the plate was selected by the colony hybridization method: The colony was transferred to a nitrocellulose filter and digested. The DNA was fixed on the filter and hybridized to the probe as described in (2). The filter was autoradiographed and a recombinant colony was selected. Additionally, the presence of a nitrile hydratase gene in the transformant was confirmed according to the Southern hybridization method.

(6) Isolation and Purification of Recombinant Plasmid and Construction of the Restriction Map of the Inserted DNA Fragments The transformant selected as described in (5) was grown in 100 ml of 2×YT medium containing 50 µg/ml of ampicillin at 37° C. overnight (12 hours). The bacterial cells were harvested and TNE was added to the cells. The cells were collected again by centrifugation, and 8 ml of STE and 10 mg of lysozyme were added to the cells. The mixture was incubated at 0° C. for five minutes. 4 ml of 0.25M EDTA, 2 ml of 10% SDS (at room temperature) and 5 ml of 5M NaCl were added to the mixture. The mixture was incubated at 0°–4° C. for three hours, and ultracentrifuged. ½ volume of 30% PEG 6000 was added to the supernatant. The mixture was incubated at 0–4° C. overnight (12 hours) and centrifuged again. TNE was added to the pellet to bring the volume up to 7.5 ml. CsCl was added to the suspension to rid of proteins. Then, 300–500 mg/ml of ethidium bromide was added to the supernatant and the mixture was transferred to a centrifuge tube. The tube was heat-sealed and ultracentrifuged. cccDNA was removed using a peristaltic pump. A bit more than equal amount of isopropyl alcohol saturated with water was added to cccDNA to remove ethidium bromide. The DNA sample was dialyzed against TE, resulting in about 3 ml of purified recombinant DNA. The recombinant plasmid thus obtained containing a 6.7 kb DNA fragment was designated as pNHJ10H (The recombinant plasmid containing a 9.4 kb DNA fragment was designated as pNHJ20L).

Figure 1A:
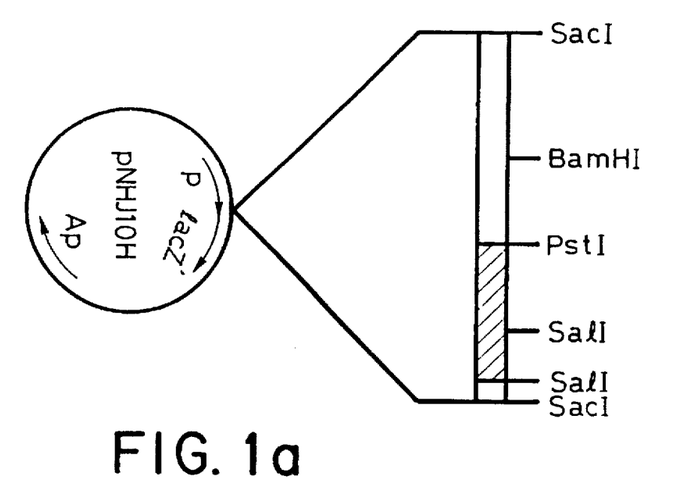
Figure 1B:
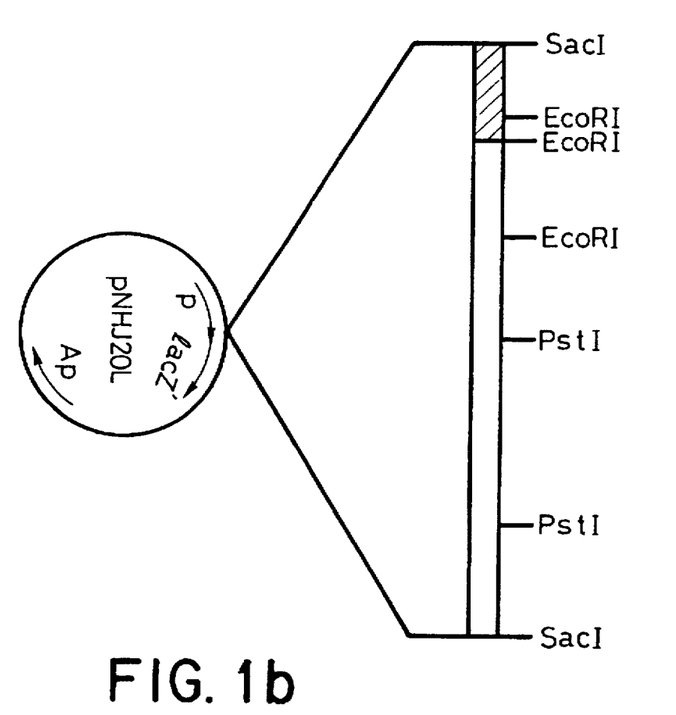

These plasmid DNAs were digested with EcoRI, BamHI, PstI, SacI and SalI. The restriction maps were constructed and are shown in FIG. 1.

(7) DNA Sequencing

The location of a nitrile hydratase gene in the DNA fragment of pNHJ10H was determined according to the restriction map constructed and to the Southern hybridization method. An extra segment in pNHJ10H was cleaved off with PstI and SalI: The 6.0 kb DNA fragment resulted in 1.97 kb. Similarly, an extra segment in pNHJ20L was cleaved off with EcoRI and SacI: The 9.4 kb DNA fragment resulted in 1.73 kb.

These DNA fragments were sequenced by the Sanger method [Sanger, F., Science 214:1205–1210 (1981)] using M13 phage vector. The nucleotide sequence of the 1.97 kb DNA fragment (pNHJ10H) and the 1.73 kb DNA fragment (pNHJ20L) are shown in the Sequence Listing by SEQ ID: No. 14 and SEQ ID: No. 15, respectively.

The amino acid sequence deduced from the nucleotide sequence was found fully identical to the amino acid sequence as determined in (1). The sequence analysis also revealed that the DNA fragment contained the sequence coding for the α- and β-subunits.

(8) Production of Nitrile Hydratase Using the Transformant and Conversion of Nitriles to Amides Using Nitrile Hydratase TG1/pNHJ10H and TG1/pNEJ20L were inoculated into 10 ml of 2×YT medium containing 50 µg/ml of ampicillin and incubated at 30° C. overnight (12 hours). 1 ml of the resultant culture was added to 100 ml of 2×YT medium (50 µg/ml of ampicillin, 0.1 g of $CoCl_2.6H_2O/l$). The mixture was incubated at 30° C. for 4 hours. IPTG was added to the mixture to a final concentration of 1 mM. The mixture was incubated at 30° C. for 10 hours. After harvesting the cells, the cells were suspended in 5 ml of 0.1M phosphate buffer (pH 7.5). The suspensions were disrupted by sonification for 5 min and centrifuged at 12,000×g for 30 min. The resulting supernatants were used for the enzyme assay. The enzyme assay was carried out in a reaction mixture (12 ml) containing 50 mM potassium phosphate buffer (pH 7.5), 6 mM benzonitrile and an appropriate amount of the enzyme. The reaction was carried out at 20° C. for 30 min and stopped by the addition of 0.2 ml 1M HCl. The amount of benzamide formed in the reaction mixture was determined by HPLC. As a control, the mixture obtained by the same procedure as described above but from *E. coli* TG1 was used. The levels of nitrile hydratase activity in cell-free extracts of *E. coli* containing pNHJ10H and pNHJ20L were $1.75 \times 10^{-3}$ and $6.99 \times 10^{-3}$ units/mg, respectively, when cultured in 2×YT medium in the presence of $CoCl_2$ and IPTG. Benzamide was found in the reaction mixture of TG1/pNHJ10H and pNHJ20L, whereas no benzamide was found in the reaction mixture of TG1. A number of references are cited herein, the disclosures of which are incorporated in their entireties, by reference herein.

What is claimed is:

1. An isolated DNA$^{(H)}$ fragment encoding a polypeptide having nitrile hydratase activity, said polypeptide consisting of a an $\alpha^{(H)}$-subunit and $\beta^{(H)}$-subunit, wherein the isolated DNA fragment consists of a 1970 kb DNA fragment having the nucleotide sequence of SEQ ID: No. 14.

2. A DNA comprising DNA$^{(H)}$ of claim 1 in a recombinant cloning vector.

3. A transformed cell containing the recombinant DNA of claim 2.

4. A method of producing nitrile hydratase which comprises culturing the transformant as claimed in claim 3 which is a prokaryote transformant and recovering nitrile hydratase from the culture.

5. A method of producing amides which comprises hydrating nitriles using nitrile hydratase obtained from the culture of the transformant of claim 3.

6. A method of producing amides which comprises culturing the transformant as claimed in claim 3, and hydrating nitriles to amides using the resultant culture, isolated bacterial cells, the supernatant of the culture, an extract of the culture, or a fixed material thereof.

7. A method of producing nitrile hydratase which comprises culturing a transformed cell containing the plasmid of claim 2, in the presence of cobalt, wherein the transformed cell is a prokaryotic cell, and recovering nitrile hydratase from the culture.

8. An isolated DNA$^{(L)}$ fragment encoding a polypeptide having nitrile hydratase activity, said polypeptide consisting of an $\alpha^{(L)}$-subunit and $\beta^{(L)}$-subunit, wherein the isolated DNA fragment consists of a 1730 kb DNA fragment having the nucleotide sequence SEQ. ID. No. 15.

9. A DNA comprising DNA$^{(L)}$ of claim 8 in a recombinant cloning vector.

10. A transformed cell containing the recombinant DNA of claim 9.

11. A method of producing nitrile hydratase which comprises culturing the transformant as claimed in claim 10 which is a prakoaryote transformant and recovering nitrile hydratase from the culture.

12. A method of producing amides which comprises hydrating nitriles using nitrile hydratase obtained from the culture of the transformant of claim 10.

13. A method of producing amides which comprises culturing the transformant as claimed in claim 10, and hydrating nitriles to amides using the resultant culture, isolated bacterial cells, the supernatant of the culture, an extract of the culture, or a fixed material thereof.

14. A method of producing nitrile hydratase which comprises culturing a transformed cell containing the DNA of claim 9, in the presence of cobalt, wherein the transformed cell is a prokaryotic cell, and recovering nitrile hydratase from the culture.

* * * * *